United States Patent
Fang et al.

(10) Patent No.: US 7,390,384 B2
(45) Date of Patent: Jun. 24, 2008

(54) DEVICE FOR PRODUCING NEGATIVELY CHARGED NANOPARTICLES AND A METHOD FOR THE SAME

(76) Inventors: Moxi Fang, Room 401, Building 904, Zhongguancun, Haidian District, Beijing, 100086 (CN); Yue Sun, Room 401, Building 904, Zhongguancun, Haidian District, Beijing, 100086 (CN)

( * ) Notice: Subject to any disclaimer, the term of this patent is extended or adjusted under 35 U.S.C. 154(b) by 672 days.

(21) Appl. No.: 10/483,843

(22) PCT Filed: May 13, 2002

(86) PCT No.: PCT/CN02/00328

§ 371 (c)(1),
(2), (4) Date: Jan. 12, 2004

(87) PCT Pub. No.: WO03/006362

PCT Pub. Date: Jan. 23, 2003

(65) Prior Publication Data

US 2004/0168923 A1     Sep. 2, 2004

(30) Foreign Application Priority Data

Jul. 11, 2001   (CN) ................................. 01 1 20188

(51) Int. Cl.
*B82B 3/00*     (2006.01)
*B01J 19/08*    (2006.01)
*A61N 1/44*     (2006.01)

(52) U.S. Cl. ..................................... 204/280; 204/229.4
(58) Field of Classification Search ................. 204/298, 204/192, 280, 229.4; 118/300; 422/186.04, 422/186; 95/29
See application file for complete search history.

(56) References Cited

U.S. PATENT DOCUMENTS

| 3,413,545 | A | * | 11/1968 | Whitby | ....................... | 324/71.1 |
| 5,247,842 | A | * | 9/1993 | Kaufman et al. | ........... | 73/865.5 |
| 6,163,098 | A | * | 12/2000 | Taylor et al. | ................ | 310/308 |

* cited by examiner

*Primary Examiner*—Roy King
*Assistant Examiner*—Jessee Roe
(74) *Attorney, Agent, or Firm*—Blakely, Sokoloff, Taylor & Zafman; Stephen M. De Klerk

(57) ABSTRACT

A device and method are provided for producing negatively charged nanoparticles. The device comprises a power supply, an electron supermicroemitter and a controller, the power supply connects with the electron supermicroemitter and the controller respectively. The potential of the electron supermicroemitter to the ground is controlled in the range of −2 kV to −29 kV by the power supply and the controller in accordance with the shape, size and different application of the materials of the emitter, so as to form field electron emitting of tunneling effect. The energy of electrons with high current density produced by the emitter can be adjusted during the electrons' colliding with particles in aerosol such that the electrons are attached to the nanoparticles of different size with wider energy band to form negatively charged nanoparticles.

4 Claims, 1 Drawing Sheet

DEVICE FOR PRODUCING NEGATIVELY CHARGED NANOPARTICLES AND A METHOD FOR THE SAME

CROSS-REFERENCE TO OTHER APPLICATIONS

This Application is a National Phase of International Application No. PCT/CN02/00328, filed on May 13, 2002, which claims priority from P.R. China Patent Application No. 01120188.6, filed on Jul. 11, 2001.

FIELD OF THE INVENTION

The present invention relates to a device and method for producing nanoparticles, specifically to a device and method for producing novel negatively charged nanoparticles by combining two particles and electric charges in bioclimatology and physics, which are unrelated with each other, to be used in fields of medicine, home appliance, aseptic engineering, freshness preservation engineering, bioengineering, and the like.

BACKGROUND OF THE INVENTION

In bioclimatology, the state of air environmental condition is called by scientific workers as the aerosol state. Molecule cluster, liquid and solid particles dispersed in air as aerosols are mostly nanoparticles.

Nanoparticles exhibit small-scale effect, surface and interfacial effect and quantum-scale effect, and have large specific surface area and big number of atoms on the surface. Surface effect and interfacial effect are intensified with decreasing particle size. The big specific surface area and the big number of atoms on the surface increase the activity of the nanoparticle greatly. Due to the small-scale effect and surface effect, nanoparticles of different size also cause variation of surface electron spin conformation and electron energy spectra distribution. Quantum-scale effect of nanoparticles results in discrete energy level. The interval between energy levels changes with the changes of the nanoparticle sizes. Nanoparticles in aerosol are composed of different particles with different sizes. Because of the above-mentioned properties, nanoparticles greatly enhanced the ability to combine with electrons of different energy levels to form a very wide energy band of electron affinity.

The problem is what kind of electron-emitting electrode can be used to achieve a strong enough electric field with narrowing potential barrier on the electrode surface. Due to the tunnel effect in quantum mechanics, electrons will penetrate and escape from the tunnel as field electron emission. How to increase the emission current density is a problem under research.

In the 1960s, electrically charged aerosol centers were established in Texas and other states in the US. By ejecting pressurized gas the atomized physiological saline and electrons were emitted at the same time in the same direction at an electric potential of 26 kV-60 kV on an ejector to form electrically charged aerosol. Such aerosol was used to cure respiratory disease. It was effective in curing bronchitis and asthma, infection of the upper respiratory tract, emphysema, laryngitis, and pharyngitis. Besides the ejector, auxiliary equipments of gas pump, and liquid transport system were required. Atomized saline particles were mostly not nanoparticles. Even under the action of 26 kV-60 kV electric field, electrically charged aerosol could only travel a distance of about 1.8 m and disappeared beyond that distance. Such electrically charged aerosol was not able to directly participate in the electric metabolism at the tissue-cell-molecule level, so the biological effect and sterilizing effect were less promising.

DISCLOSURE OF THE INVENTION

The object of the present invention is to adopt an electron supermicroemitter at a micron-level or sub micron-level to provide very high emitter current density. When the electrode surface has a strong enough electric field, the potential barrier of electrode will narrow and electrons on the electrode will penetrate and escape from the tunnel because of tunnel effect in quantum mechanics to form field emission electrons, which can provide a very high emission current density.

The present invention is to combine the physical characteristics of nanoparticles and the tunnel effect in quantum mechanics. When the electrons 'e' emitted by the electron emitting electrode collide with the particles in aerosol, the electrons can adjust the energy and adhere to the nanoparticles 'Nm' with a broad energy band of electron affinity to form new negatively charged nanoparticles '$N^-m$', that is to realize: $e + Nm \rightarrow N^-m$.

Generally, there exist a few particles with different electric charges in air. Particles with and without electric charge can attract with each other and coalesce, resulting in combination of opposite charges and fall-off in large particles with the electric charge disappearing upon contact with ground. The negatively charged nanoparticles produced by the present invention appear in a large amount in a certain scope with same electric charges repelling each other. Scientists of bioclimatology and physics all think that such state of system is more stable.

Such novel particles produced by using the physical characteristics and tunnel effect in quantum mechanics of nanoparticles inevitably leads to exclusively negatively charged nanoparticles without the presence of any other compounds or impurities.

The device for producing negatively charged nanoparticles of the present invention comprises a power supply, a casing, a controller and an electrode with only one potential, that is, an electron supermicroemitter, wherein, the power supply connects with the electron supermicroemitter and the controller respectively, and the potential of the electron supermicroemitter to the ground is controlled in the range of −2 kV to −29 kV.

The said electron supermicroemitters are those with an electrode of an emitting body having a dimension at a micron level or sub-micron level. The material for preparing the said electron supermicroemitter of the present invention is platinum, gold, rhenium, iridium, tungsten or carbon fiber or their combination, or alloys with platinum, gold, rhenium, iridium and/or tungsten as the main components. The shape of the electrode could be any one or combination of the shapes selected from the group consisting of disk, cylinder, saw teeth, needle, sharp-ended, sphere, spheroid, arc, ring, bar, etc. The electron supermicroemitter could be a single electrode or multiple electrodes. The dimension of the electron supermicroemitter is ≦100 micron.

The method for producing negatively charged nanoparticles according to the present invention is as follows. The negatively charged nanoparticles producing device constructed by connecting the power supply with the electron supermicroemitter and the controller respectively is used. The potential of the nanoparticles in air and the electron supermicroemitter to the ground, under the action of the power supply and the controller, are controlled in the range of −2 kV to −29 kV. Electrons emitted by tunnel effect combines with the nanoparticles to produce new negatively charged nanoparticles. The electric potential range is determined by the material, shape, and dimension of the electrode and the different application equipment as used.

Field emission by tunnel effect generates electrons 'e' of high electric current density, which upon colliding with particles in aerosol, can adjust the energy (for example, electrons of high energy can lose its energy or reduce its energy on collision) and adhere on nanoparticles 'Nm' of different sizes with a broad energy band (The nanoparticles in air consist of various molecule clusters—either in the solid state, liquid state or gaseous state—and nanoparticles of different sizes ($10^{-7}$–$10^{-9}$ m).). The reaction is as follows:

$$e+Nm \rightarrow N^{-}m$$

Negatively charged nanoparticles are thereby produced. Under the action of electric field at any potential in the range of −2 kV to −29 kV, these particles can rapidly diffuse outward to cover a certain area.

The said electron supermicroemitter can be made according to one of the following methods:

a) Platinum, gold, or carbon fiber filament is fixed on a glass carriage by a soldering method. The leading-out end is made by bonding platinum, gold, or carbon fiber to copper wire with conducting glue (such as a conducting glue made of silver powder and epoxy resin). Platinum wire can be connected to the conductor with indium melted at a low temperature.

b) Platinum, gold, rhenium, tungsten, iridium or carbon fiber filament is bonded and sealed in a carriage made of insulators made of quartz, glass, PE, PTFE (plastics), polyester fiber, silicon nitride, alumina (porcelain) with epoxy resin adhesive. The leading-out end is made by bonding platinum, gold, rhenium, tungsten, iridium or carbon fiber filament to copper wire with conducting glue (such as a conducting glue made of silver powder and epoxy resin). Fixation of the leading-end and the conductor can follow the same procedures as mentioned in method "a".

c) Platinum, gold, rhenium, tungsten, iridium or carbon fiber filament is arranged on the surface of an insulator in such shapes as bar, ring, arc, etc. It is then fixed and bonded with adhesive, such as epoxy resin. Fixation of the insulator, the leading-out end and the conductor can follow the same procedures as mentioned in methods "a" and "b".

d) Rhenium, tungsten or its corresponding alloy are made into electrodes of various shapes by electrolytic corrosion, such as the sharp-ended shape, needle shape, saw teeth shape, etc. In regard to the electrolytic corrosion, it has been taught in various common textbooks or literatures. The electrode made hereby is fixed on an insulator carriage with epoxy resin or riveted on an insulator carriage. According to the method of fixation, the insulator can be quartz, glass, PE, PTFE (plastics), silicon nitride, alumina (porcelain), polyester composite plate, etc. The leading-out end can be bonded to the conductor with conducting glue, or the leading-out wire and the electrode can be fixed on an insulator at the same time by mechanical means. The connection is illustrated by the following two examples. There are options for fixing and leading-out of the saw-teeth shaped electrode. One is the use of an epoxy resin and conducting glue. Saw teeth electrode is bonded with an epoxy resin to the insulator located underneath with one side of electrode connected to leading-out wire with conducting glue. The other is mechanical means. According to the mechanical means, saw teeth electrode is fastened with rivets on an insulator by clamps on both sides and the leading-out wire is riveted with a clamp on one side of the electrode.

The sharp-ended and needle electrode can also use the above options except for some specific structure. For example, fixing clamp is not required for the needle electrode. A pin sleeve or rivet sleeve is used to fasten the electrode and lead wire directly on the insulator.

e) Photoetching can be used to make electron supermicroemitter. According to this method, a uniform metallic film is coated on an insulator plate by spraying or sputtering. The metal film can be made of platinum, gold, iridium, etc. A photosensitive polymer film of polyimide is coated on the metallic film, and photoetching is carried out to form an electrode with a required shape. The matrix material of the electrode can be $Si/SiO_2$, quartz, glass, silicon nitride, etc. Leading-out wire is made by bonding the electrode to copper wire with conducting glue.

The sizes of the negatively charged nanoparticles are smaller than those of red blood cells in blood and ordinary bacteria, and are a fraction of the latter or even much smaller. Such nanoparticles can enter human body through respiration and skin mucous membrane into the lung and blood circulation and release electric charge. The equilibrium state of electric charges on cell wall can be improved to form bioelectricity having direct biological effect on physiological condition, tissue cells and metabolism of human body.

Negatively charged nanoparticles in human body can directly participate in electro-metabolism at tissue-cell-molecule level, promoting transform of bio-electricity, adjusting electric potential equilibrium of organism, and improving natural physiological condition and biochemical environment of human body. The non-specific and broad-spectrum medical effect is achieved through the adjusting function of nerve-humor.

Negatively charged nanoparticles with apparent biological effect have apparent conditioning opsonic function on neural system, cardiovascular system, respiratory system, urinary system and digestive system and have curative effect on many diseases. Clinical application of the negatively charged nanoparticles has caught wide attention.

Experimental studies demonstrate that, due to the quantum mechanics characteristics, the negatively charged nanoparticles can rapidly cover a certain scope and strongly inhibit the growth of and eradicate such harmful bacteria and viruses as *Pseudomonas aeruginosa*, syphilis spirochete, staphylococcus, bacillus coli, mycosis, Monilia, etc.

It is well known that research and application of bioelectricity have been developing continuously. Clinical application of electroencephalogram (EEG), electrocardiogram (ECG), electrogastrogram (EGG) has saved the lives of countless people. Just like the clinical application of physical medical diagnosis equipment, the computerized tomography (CT), brightness type ultrasonic diagnostic apparatus, nuclear magnetic resonance apparatus, and positive electron tomography have opened a new era for the uninterrupted development of clinical diagnosis. Bioelectricity of negatively charged nanoparticles will create many new techniques and new equipment, especially in clinical treatment.

Therefore, bioelectricity of negatively charged nanoparticles can be widely used in physical medical equipment, home appliance, bioengineering, freshness preservation engineering, aseptic engineering and environmental condition improvements.

BEST MODE FOR CARRYING OUT THE INVENTION

Figure 1:
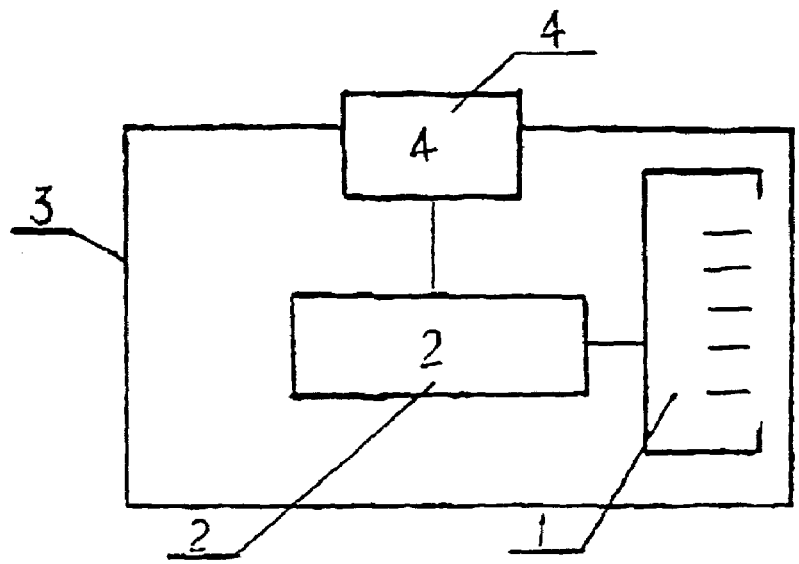
FIG. 1 is the block diagram showing the principle of the present invention.

As shown in FIG. 1, the device of the present invention comprises basic component parts of an electron supermicroemitter 1, a power supply 2, a casing 3, and a controller 4. Other parts can be added according to the usage and device, such as multi-functions carriage or turntable. The present invention can also be combined with other device to form a new equipment with new functions, with its control device compatible with other parts of the control equipment.

According to the purpose of application and the function of product, the electron supermicroemitter can be a single electrode, multiple electrodes or a combination electrode. The device casing can be designed as one with totally different shape, function and configuration, as the potential of the electron supermicroemitter to the ground is controlled in the range of −2 kV to −29 kV, depending on its structure, dimension, shape and material, and purpose of application.

Figure 2:
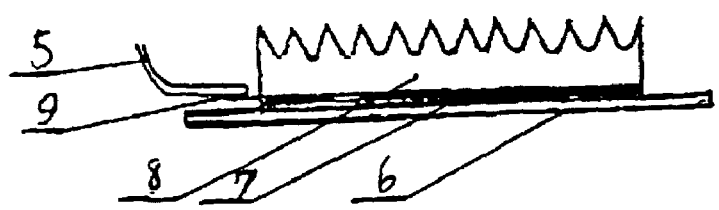
FIG. 2 is the schematic drawing of the leading-out for the saw teeth electrode bonded with epoxy resin and conducting glue.

As shown in FIG. 2, epoxy resin and conducting glue are used to fix and leading-out the electrode. Saw teeth electrode 8 is bonded underneath to the insulator 6 by epoxy resin 7, and leading-out wire is made of a conductor 5 bonded to one end of the electrode 8 with conducting glue 9.

Figure 3:
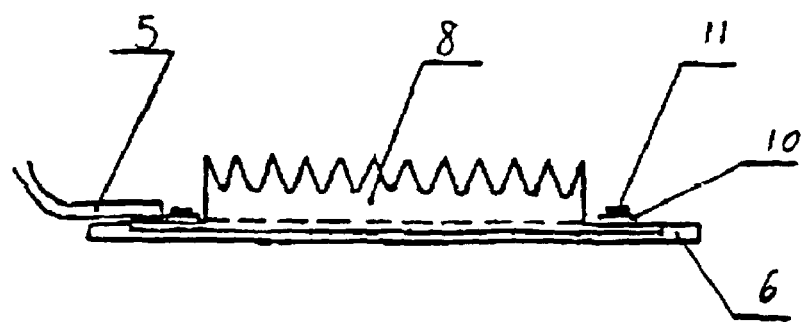
FIG. 3 is the schematic drawing of the leading-out for the saw teeth electrode fastened with mechanical means.

As shown in FIG. 3, mechanical means is used to fasten and leading-out the electrode. Saw teeth electrode 8 is fastened with an insulator 6 by a clamp 10 and a rivet 11. Leading-out wire 5 is fastened with the clamp 10 and the rivet 11.

The invention claimed is:

1. A device for generating negatively charged nanoparticles, which is comprised of a power supply, a casing, a controller and an electron-emitter, the power supply is connected with the electron-emitter and the controller respectively; characterized in that the electron-emitter is an electron supermicroemitter, dimensions of an emitting part of the electron supermicroemitter being smaller than or equal to a micron level; there is only one electrode with one potential in the electron supermicroemitter; the electron supermicroemitter emits electrons by means of tunneling effect, and the emitted electrons combine with the nanoparticles in air to form negatively charged nanoparticles; the potential of the electron supermicroemitter to the ground is controlled in a range of −2 kV to −29 kV.

2. The device as claimed in claim 1, characterized in that the electron supermicroemitter is comprised of a single or multiple electrodes, a shape of the electrode is any one or combination of the shapes selected from the group consisting of disk, cylinder, saw teeth, needle, sharp-ended, sphere, spheroid, arc, ring, and bar.

3. The device as claimed in claim 1, characterized in that the electron supermicroemitter is made of platinum, gold, rhenium, iridium, tungsten or carbon fiber or their combination or an alloy with platinum, gold, rhenium, iridium and/or tungsten as a main component.

4. The device as claimed in claim 1, characterized in that the electron supermicroemitter is made according to one of the following methods:
   a) platinum, gold, or carbon fiber filament is fixed on a glass carriage by a soldering method, a leading-out end is made by bonding platinum, gold, or carbon fiber filament to copper wire with conducting glue, platinum wire can also be connected with copper wire by indium melted at a low temperature;
   b) platinum, gold, rhenium, tungsten, iridium or carbon fiber filament is bonded and sealed in a carriage made of insulators of quartz, glass, PE, PTFE, polyester fiber, silicon nitride, and/or alumina (porcelain) with epoxy resin adhesive, the leading-out end is made by bonding platinum, gold, rhenium, tungsten, iridium or carbon fiber to copper wire with conducting glue;
   c) platinum, gold, rhenium, tungsten, iridium or carbon fiber filament is arranged on the surface of an insulator made of quartz, glass, PE, PTFE, polyester fiber, silicon nitride and/or alumina in a required shape, it is then fixed and bonded with adhesive, platinum, gold, rhenium, tungsten, iridium or carbon filament is bonded to copper wire with conducting glue as leading-out end;
   d) rhenium, tungsten or their corresponding alloy is made into electron supermicroemitters of various shapes by electrolytic corrosion, the said electron supermicroemitter is fixed on an insulator carriage with epoxy resin or riveted on insulator carriage by mechanical means, the insulator can be any one of quartz, glass, PE, PTFE, silicon nitride, alumina, polyester composite plate, the leading-out end can be bonded to conductor with conducting glue, or a lead conductor and electrode can be fixed on insulator at the same time by mechanical means, such method likewise applies to a sharp-ended and needle electrode; or
   e) photoetching is utilized to make electron supermicroemitter: a uniform metallic film is coated on an insulator plate by spraying or sputtering, the metallic film can be platinum, gold, iridium, a photosensitive polymer film of polyimide is coated the metallic film and photoetching is carried out to form electrode of a required shape, a matrix material of the electrode can be any one of $Si/SiO_2$, quartz, glass, silicon nitride, leading-out wire is made by bonding electrode to copper wire with conducting glue.

* * * * *